United States Patent
David et al.

(10) Patent No.: US 6,761,694 B2
(45) Date of Patent: Jul. 13, 2004

(54) METHODS FOR MEASURING RETINAL DAMAGE

(75) Inventors: Robert David, Newport Beach, CA (US); Michael Belkin, Givat Shmuel (IL)

(73) Assignee: Allergan, Inc., Irvine, CA (US)

( * ) Notice: Subject to any disclaimer, the term of this patent is extended or adjusted under 35 U.S.C. 154(b) by 80 days.

(21) Appl. No.: 10/016,036

(22) Filed: Dec. 13, 2001

(65) Prior Publication Data

US 2003/0114772 A1 Jun. 19, 2003

(51) Int. Cl.$^7$ ............................................. A61B 13/00
(52) U.S. Cl. ..................................................... 600/558
(58) Field of Search ............................... 600/558, 561, 600/486; 351/200; 424/427, 423

(56) References Cited

U.S. PATENT DOCUMENTS

| | | | |
|---|---|---|---|
| 5,667,968 A | 9/1997 | LaVail et al. | 514/12 |
| 5,722,970 A | 3/1998 | Colvard et al. | 606/3 |
| 5,980,929 A | * 11/1999 | de Juan, Jr. | 424/427 |
| 6,090,102 A | 7/2000 | Telfair et al. | 606/10 |
| 6,129,682 A | * 10/2000 | Borchert et al. | 600/561 |
| 6,135,998 A | 10/2000 | Palanker | 606/39 |
| 6,225,303 B1 | 5/2001 | Miller et al. | 514/185 |
| 6,248,741 B1 | 6/2001 | Wheeler et al. | 514/249 |
| 6,267,477 B1 | 7/2001 | Karpol et al. | 351/221 |

OTHER PUBLICATIONS

Zuclich et al., "Retinal damage induced by red diode laser", *Health Physics*, Jul. 2001, 81(1):8–14.

Chuang et al., "A traumatic macular hole secondary to a high–energy Nd:YAG laser", *Ophthalmicd Surgery and Lasers*, Jan./Feb. 2001, 32(1):73–76.

Robertson et al., "Laser pointers and the human eye", *Arch. Ophthalmol.*, Dec. 2000, 118:1686–1691.

Mainster, "Decreasing retinal photocoagulation damage: principles and techniques", *Seminars in Ophthalmology*, Dec. 1999, 14(4):200–209.

Roider et al., "Macular injury by a military range finder", *Retina*, 1999, 19:531–535.

Rosner et al., "Neuroprotective therapy for argon–laser induced retinal injury", *Exp. Eye Res.*, 1997, 65:485–495.

Solberg et al., "MK–801 has neuroprotective and antiproliferative effects in retinal laser injury", *Investigative Ophthalmology & Visual Science*, Jun. 1997, 38(7):1380–1389.

Shapira, "Talia technology and the retinal thickness analyzer (RTA)", Mar. 2000, pp. 1–16.

Ciancaglini et al., "Reproducibility of retinal thickness analyzer measurements in healthy and glaucomatous subjects", Abstract. Exact publication date is unknown. Printed Aug. 30, 2001.

Koozekanani et al., "Retinal thickness measurements in optical coherence tomography using a Markov boundary model", 2000, Abstract.

"New eye care instruments", 4 pages from the University of Illinoic at Chicago web site (http://www.uic.edu/com/eye/education/eyefacts/newinstruments.htm). Publication date is unknown. Printed Aug. 30, 2001.

* cited by examiner

*Primary Examiner*—Max F. Hindenburg
*Assistant Examiner*—Brian Szmal
(74) *Attorney, Agent, or Firm*—Stout, Uxa, Buyan & Mullins, LLP; Frank J. Uxa; Greg S. Aollrigel

(57) ABSTRACT

Methods for measuring retinal damage resulting from an injury include calculating the slope of retinal thickness from the injury site to the periphery of the site. A shallower slope of retinal thickness correlates with a greater degree of damage resulting from the injury. The methods may also be useful to screen pharmaceuticals for potential neuroprotective effects against retinal injuries.

17 Claims, 1 Drawing Sheet

METHODS FOR MEASURING RETINAL DAMAGE

BACKGROUND

This invention relates to methods of measuring retinal damage. In particular, the invention relates to methods of measuring retinal damage in situ by measuring changes in retinal thickness resulting from such damage.

The human retina includes three primary nuclear layers that include five major classes of neurons. The five major classes of neurons are: (i) photoreceptors (rods and cones); (ii) bipolar cells; (iii) horizontal cells; (iv) amacrine cells; and (v) ganglion cells. The outer nuclear layer (ONL) contains the photoreceptor cell bodies. The inner nuclear layer (INL) contains the cell bodies of the bipolar neurons, horizontal neurons, and amacrine neurons. Interplexiform neurons, displaced ganglion cells, throughout the glial cells of Müller are also located in the INL. The ganglion cell layer contains the cell bodies of most of the ganglion cells, displaced amacrine cells, and some astroglial cells.

Synaptic connections are made among the various classes of neurons, which result in the vertical and lateral flow of visual information in the retina. Both excitatory and inhibitory synaptic connections are present in the retina. Glutamate is probably the primary excitatory neurotransmitter. Gamma-aminobutyric acid (GABA) is probably a major inhibitory neurotransmitter. Other neurotransmitters are present among the various retinal neurons.

Lasers are increasingly being used in research, medical, industrial, and military fields. Eye exposure to lasers may be accidental or intended. For example, ophthalmic laser treatment is a treatment for many conditions of the eye, including age-related macular degeneration (AMD), macular edema, and photorefractive keratectomy (PRK). In addition, a number of diseases that involve macular degeneration that are potentially treated with lasers include Stargardt's disease, Best's disease, Batten's disease, Sjogren-Larsson syndrome, cone-rod dystrophy, and ovine ceroid lipofuscinosise, and Tay-Sach's disease. At least some types of AMD are caused by increased neovascularization.

Laser photocoagulation treatment utilizes thermal energy to destroy neovascular tissue. The energy of the laser heats the tissue and results in full-thickness retinal damage including secondary, collateral damage to the tissue surrounding the laser contact site. The secondary, collateral damage may result from physiological effects, such as excessive release of the neurotransmitter, glutamate, resulting from the primary damage caused by the laser (Marshall et al., "Histopathology of ruby and argon laser lesions in monkey and human retina. A comparative study", *Br. J. Ophthalmol.*, 59(11):610–630 (1975); Rosner et al., "Neuroprotective therapy for argon-laser induced retinal injury", *Exp. Eye Res.*, 65:485–495 (1997)). Additionally, the secondary, collateral damage may be attributed to phospholipid hydrolysis and arachidonic acid metabolites, oxygen free radicals, changes in intracellular and extracellular ion concentrations, and other excitotoxic mechanisms. The secondary damage may exacerbate the primary anatomical and physiological damage caused by the laser and may result in unwanted side effects, such as further vision loss, of the subject exposed to the laser.

Retinal damage caused by lasers is conventionally assessed ophthalmoscopically using opthalmoscopes slit lamps and/or retinal photographs ("fundus photos"). Using ophthalmoscopes, retinal lesions produced by lasers may be measured by viewing the diameter and intensity of the lesion(s) on the retina. Because light energy from a laser is converted into thermal energy by light absorption of the retinal pigment epithelium and choroid, the retina is damaged by the heat conduction, and the thermally-injured retina loses its transparency and scatters white light back to the observer. Greater primary damage correlates with less transparency and a whiter lesion. When fundus photos are utilized, a physician may inject a fluorescent drug (such as flouroscein) into a patient's blood, and allow enough time for the drug to circulate throughout the patient's blood vessels and capillaries. The physician then uses topical eye drops to dilate the pupil, and takes a magnified photograph ("angiogram") of the retina, using an ultraviolet light source with a wavelength that causes the drug in the patient's blood to emit fluorescent light at a different wavelength from the light source. Lesions are characterized by fluorescent regions corresponding to blood vessels that have been exposed resulting from the thinning or removal of the overlying retinal tissue.

Lesions can be classified in a number of ways (see, for example, Mainster, Decreasing retinal photocoagulation damage: principles and techniques", *Seminars in Ophthalmology*, 14(4):200–209 (1999)). Lesions can be classified by their appearance at the time of laser treatment, ranging from faint to intense white. Lesions can also be classified by how they are observed (e.g. angiographically versus ophthalmoscopically). Lesions can also be classified by their latency from injury. In addition, retinal lesions have been examined histopathologically (Rosner, et al., Neuroprotective therapy for argon-laser induced retinal injury, *Exp. Eye Res.* 65:485–495 (1997); Robertson et al., Laser pointers and the human eye, A clinicopathologic study, *Arch Ophthalmol.*, 118:1686–1691 (December 2000); Zuclich et al., Retinal damage induced by red diode laser, *Health Phys.*, 81(1):8–14 (2001)).

Conventional in situ methods of estimating retinal damage evaluate the primary damage caused by the laser (i.e., the diameter of the lesion as seen by the "whiteness" of the lesion, or by the fluorescence of the lesion). The conventional in situ methods do not measure the secondary, collateral damage resulting from laser injuries. The secondary damage caused by the laser has only been estimated histopathologically (e.g., Rosner et al., supra); however, histopathological examination is not suitable for patients.

Therefore, there remains a need for an in situ method for measuring retinal damage, including secondary retinal damage, resulting from a retinal injury. Such a method will not only provide the ability to quantify retinal damage, including secondary retinal damage, resulting from focal injuries, such as laser injuries, but will also be useful for screening pharmaceutical agents for neuroprotective effects against such damage.

SUMMARY OF THE INVENTION

The present invention meets this need and provides a method for measuring retinal damage in situ. The methods of the invention enable one to measure or quantify the amount of damage caused by retinal injury without removing an eye or eyes from a subject so injured. In addition, the methods of the invention provide an in situ method for determining neuroprotective effects of ophthalmic solutions.

In one embodiment of the invention, a method for measuring retinal damage resulting from a focal injury to a retina comprises the step of calculating a slope of retinal thickness between a plurality of locations of the retina. In one embodiment of the invention, the focal injury is caused by a laser.

In another embodiment of the invention, a method for measuring retinal damage caused by a laser comprises the steps of: (i) measuring the thickness of the retina, which has been exposed to a laser, at a plurality of locations on the retina; and (ii) calculating the slope of retinal thickness from the site exposed to the laser to an unaffected site.

In a further embodiment of the invention, a method for measuring retinal damage may comprise measuring and calculating the average retinal thickness in the laser-induced lesion area and the surrounding retina.

In practicing the foregoing methods, retinal thickness is preferably measured in situ. A greater amount of retinal damage corresponds to a more shallow slope of retinal thickness. In addition, the retinal damage measured by the foregoing methods comprises secondary damage from the focal injury. The retinal thickness may be measured after acute inflammation produced by the injury has subsided.

The foregoing methods may also comprise an additional step of administering a neuroprotective agent to a subject. The neuroprotective effects of the agent correlate with an increased slope of retinal thickness from the site of injury to the periphery of the injury as compared to the slope of retinal thickness in a subject that has not received the neuroprotective agent. In certain embodiments, the neuroprotective agent is administered before the injury, such as when a laser causes a retinal lesion. The neuroprotective agent used in the foregoing method may reduce excitotoxicity, or may reduce secondary retinal cell death resulting from the laser injury.

Alternatively, the foregoing methods may be useful for screening pharmaceutical compositions for neuroprotective effects. Such methods comprise the step of administering a potential neuroprotective agent to a subject. The neuroprotective effects of the potential neuroprotective agent correlate with an increased slope of retinal thickness as compared to the slope of retinal thickness of an injured retina of a subject that has not received a neuroprotective agent.

In still a further embodiment of the invention, a method for determining neuroprotective effects of a compound, such as a compound in an opthalmic solution, comprises the steps of: (i) administering a potential neuroprotective agent in an ophthalmic composition to a subject; (ii) measuring the thickness of a retina, which has been exposed to a laser, at a plurality of locations of the retina; and (iii) calculating the slope of retinal thickness from the lesion of the laser to the periphery of the lesion.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

DETAILED DESCRIPTION

Figure 1:
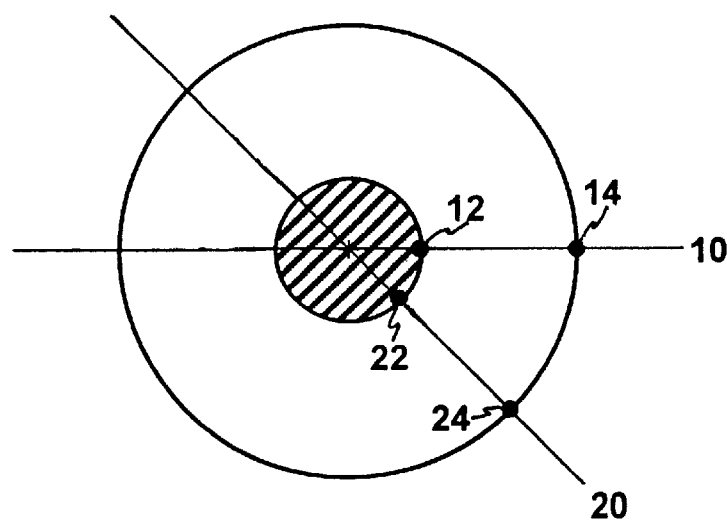
FIG. 1 is an example of a plan view of a retinal lesion caused by a focal injury.

Unless defined otherwise, all technical and scientific terms used herein have the same meaning as commonly understood by those of ordinary skill in the art to which this invention belongs. For purposes of the present invention, the following terms are defined below.

As used herein, "retinal damage" is tissue damage experienced by a retina following an injury, such as a laser injury. Retinal damage encompasses both the primary damage directly caused by the injury as well as secondary damage resulting from the injury. In addition, retinal damage encompasses cellular damage, which may include cellular injury and or cell death. Retinal damage may be characterized by anatomical, biochemical, or electrophysiological changes in the retina. As disclosed herein, retinal damage is preferably characterized by in situ methods such as by measuring changes in retinal thickness.

As used herein, "primary damage" is damage directly caused by an injury. Primary damage typically occurs at the time of injury, and therefore, is typically evident at, or soon after (within minutes or hours), the injury. Primary damage may be characterized by tissue disruption, immediate cell death, and immediate proliferation of phagocytic cells. In some embodiments of the invention, primary damage corresponds to a region of the retina that has been injured, and that no longer has normal retinal tissue.

As used herein, "secondary damage" refers to all types of damage that are not primary damage. Secondary damage may result from phospholipid hydrolysis and arachidonic acid metabolites, oxygen free radicals, changes in intracellular and extracellular ion concentrations, and excitotoxic mechanisms. Secondary damage typically is a process that occurs some time (for example, 24 hours or more) after the injury, and may be characterized by progressive tissue loss, prolonged cell death, such as neuronal cell death, and a spread of phagocytic cells. Secondary damage extends beyond the perimeter of primary damage.

As used herein, "focal injury" is a retinal injury that directly affects a clearly defined area. In other words, primary damage caused by a focal injury is well characterized and easily delineated from non-injured tissue. An example of a focal injury is a lesion caused by a laser. Other focal injuries may include physical or chemical injuries. An example of a physical injury may include a puncture or incision of the retina. Physical injuries may also be caused by electrosurgical operations near the retina. Chemical injuries may be caused by application of caustic chemicals to areas on or near the retina.

As used herein, "slope of retinal thickness" is the change in retinal thickness as a function of distance between two or more locations on the retina. The slope of retinal thickness correlates with the amount of secondary damage resulting from the retinal injury. A steep slope indicates relatively little secondary retinal damage. A shallow slope (e.g., a value approaching zero) indicates relatively greater secondary retinal damage.

As used herein, "administering" means to give or apply an agent to a subject. In certain embodiments of the invention, the agent is locally administered (e.g., non-systemically). In some embodiments of the invention, the agent will be administered to the eye, such as by intraocular injection or topical application, such as by an ophthalmic solution. Topical ophthalmic preparations, for example, ocular drops, gels, or creams, are preferable because of the ease of application, ease of dose delivery, and fewer systemic side effects.

As used herein, a "neuroprotective agent" is an agent that prevents neuronal cell death. Neuroprotective agents preferably preserve the cellular, biochemical, and physiological properties of the neurons. Examples of neuroprotective agents include anti-excitotoxic agents, such as glutamate receptor (e.g., NMDA receptor) modulators (such as, MK-801, N4K-801, memantine), calcium channel blockers, and inhibitory receptor modulators (such as GABA receptor agonists, including, but not limited to, anesthetics, such as barbiturates; benzodiazepines, such as zolpidem; and alcohol, such as ethanol). Anti-excitotoxic agents preferably reduce or prevent excessive increases in intracellular calcium concentration. Neuroprotective agents also include adenosine receptor modulators, adrenergic receptor modulators (such as, α2-receptor agonists, brimonidine, beta-blockers, etc.), glutamate uptake modulators, dopamine receptor modulators, ion channel modulators (such as, sodium or hydrogen), downstream intracellular signal modulators (such as, COP-1), prostaglandins (such as EP2 agonists), ryanodine receptor agonists (calcium release from intracellular stores), cytokines, neurotrophic and/or nerve growth factors, such as nerve growth factor (NGF) including NGFα, brain derived neurotrophic factor (BDNF), ciliary neurotrophic factor (CNTF), bone-derived growth factor (BDGF), neurotrophin-3 (NT3), neurotrophin-4/5 (NT-4/5), pigment epithelium derived factor, vitamin C, steroids, non-steroidals, cyclosporins, drugs that are active in ischemia/reperfusion assays, monoamine oxidase inhibitors (MAOIs), carbonic anhydrase inhibitors (such as acetazolamide), pump inhibitors (such as, amiloride), free-radical scavengers, nitric oxide synthetase inhibitors, and hormones.

As used herein, "potential neuroprotective agents" are agents that may have neuroprotective effects. Potential neuroprotective agents may be screened using the methods of the invention, as described herein, to assess the agents' neuroprotective effects.

The present invention is related to the discovery that retinal damage caused by a focal injury can be determined by measuring changes in retinal thickness in situ. In particular, the invention relates to the unexpected discovery that damage caused by a focal injury results in a change of retinal thickness extending from the injured site to the periphery of the injured site that can be measured as a slope (e.g., the change in retinal thickness as a function of distance between two or more locations on the retina).

The inventors have discovered that after a retinal injury, such as a laser injury, the retinal tissue that is peripheral to the area of primary damage (i.e., the peripheral tissue to the injured or lesion site) undergoes thinning as cell death spreads due to secondary, collateral effects resulting from the injury and primary damage. As cells die, the tissue thins. Increased cell death corresponds to increased tissue thinning. The degree of secondary damage (e.g., cell death) declines with distance from the injured site. The outer periphery of secondary damage accordingly corresponds to a region of the retina that has a retinal thickness similar or identical to an uninjured region of the retina. Surprisingly, the decline in secondary damage from the injured site to the periphery can be reliably measured, or quantified, as a slope (i.e., a change in retinal thickness over a predetermined distance). Illustratively, tissue damage resulting from a laser, for example, can be viewed as a crater-shaped hole. The primary damage caused by the laser corresponds to the center of the crater, and the secondary damage of the tissue corresponds to the sloped edges of the crater (see FIGS. 1 and 2, for example).

The slope of retinal thickness also surprisingly correlates with the degree of secondary damage caused by the injury. For example, a relatively intense injury will cause large primary damage, and extensive secondary damage characterized by extensive cell death and thinning of retinal tissue. Because the secondary damage extends relatively far from the lesion, the slope of retinal thickness resulting from such an injury would accordingly be small (e.g., the slope would approach zero). Small or shallow slopes correspond to increased damage because the retinal thickness changes relatively little over a given distance. In comparison, a relatively minor injury will cause some primary retinal damage, and relatively little secondary damage. Accordingly, the retinal tissue will not have experienced much thinning, and the slope of retinal thickness resulting from a relatively minor injury will be relatively large or steep.

In order to calculate the slope of retinal thickness, the thickness of the retina must be measured. In practicing the methods of the invention, it is preferred that the retinal thickness be measured in situ as compared to histologically. Retinal thickness may be measured using publicly available devices generally configured to image optical cross-sections of the retina, and to digitally process the cross-sections to result in a measurement of retinal thickness. One such device used to practice the methods of the invention is the Retinal Thickness Analyzer (RTA; Talia Technology, Ltd., Mevasseret Zion, Israel) as disclosed in U.S. Pat. No. 6,267,477, entitled, "Three dimensional imaging apparatus and a method for use thereof". Another device that may be used to measure retinal thickness in the methods of the invention is the Optical Coherence Tomography (OCT) Scanner (Humphrey Instruments, Inc., San Leandro, Calif.) and as described in U.S. Pat. No. 5,491,524, entitled, "Optical coherence tomography corneal mapping apparatus". Another device that may be used to measure retinal thickness in practicing the methods of the invention is the Heidelberg Retina Tomograph (HRT; Heidelberg Engineering GmbH, Heidelberg, Germany) and as described in U.S. Pat. No. 5,170,276, entitled, "Apparatus for imaging an object".

The images obtained by such devices can then be examined, and the slope of retinal thickness measured. The slope of retinal thickness may be calculated as a ratio by measuring the change in retinal thickness as a function of distance between two or more points of the retina near the lesion site. The human retina is approximately 200–250 µm thick. Using the devices described above, it is possible to optically cross-section the retina in 20 µm increments. If the retinal thickness changes by 200 µm over a distance of 20 µm, the corresponding slope of retinal thickness would be 10. Similarly, if the retinal thickness changes 200 µm over a distance of 2 mm, the corresponding slope would be 0.1. In the foregoing examples, a slope of 10 indicates the retinal damage is less than the retinal damage where the slope of damage is 0.1. Persons skilled in the art will appreciate that the slope of retinal thickness may be calculated over any number of distances, and that the smallest distance is only limited by the resolution of the devices used to practice the methods of the invention.

Figure 2:
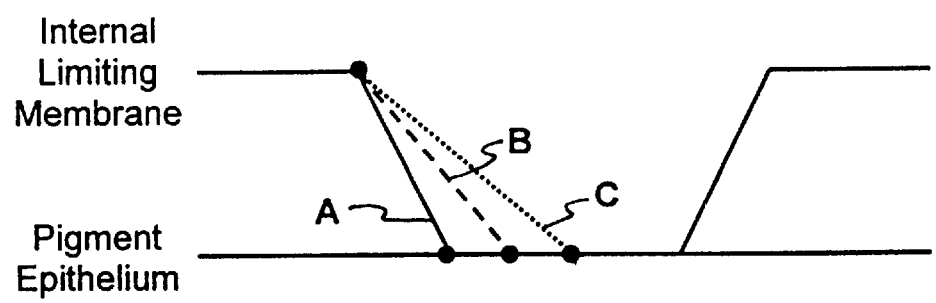
FIG. 2 is an example of a side-elevation view of a retinal lesion caused by a focal injury.

As illustrated in FIGS. 1 and 2, the slope of retinal thickness resulting from an injury may be measured from many locations. FIG. 1 is an illustrative example of a lesion created by a focal injury, such as a laser injury. The primary damage corresponds to the inner, hatched circle. The secondary damage corresponds to region perimetrically surrounding the inner, hatched circle. As illustrated in FIG. 1, the slope of retinal thickness may be measured from a point (12 or 22) near the outer edge of the area of primary damage to a point (14 or 24, respectively) near the outer edge, or periphery, of the area of secondary damage. When calculating the slope, it may be preferable to calculate the slope with radial lines extending through the aforementioned points. As used herein, a radial line is a line that extends through the center, or approximate center, of the lesion. As illustrated in FIG. 1, lines 10 and 20 are examples of radial lines.

FIG. 2 is an illustrative example of a side view of a lesion created by a focal injury. As shown in FIG. 2, the slope of retinal thickness may be calculated between two points at different positions with respect to the lesion. In one embodiment of the invention, the slope is measured along a line (line A) that tracks, or substantially tracks, the edge of retinal tissue extending from the primary lesion site to the periphery of the lesion. In another embodiment of the invention, the slope of retinal thickness may be calculated along a line (line C) extending from the center of the lesion site to the periphery of the lesion. In a further embodiment of the invention, the slope of retinal thickness may be calculated along a line (line B) extending from a point between the center of the lesion site and the edge of the lesion site where retinal tissue is present. In still further embodiments of the invention, the slope of retinal thickness may be calculated from a line extending through two or more points where retinal tissue is present. In practicing the methods of the invention, it may be desirable for one of the points to be used in calculating the slope to be positioned at the outer edge of the lesion corresponding to the outer perimeter of the zone of secondary damage, as illustrated in FIGS. 1 and 2.

As persons skilled in the art understand, when determining the slope of retinal thickness, care should be taken to measure the change in retinal thickness over a distance where the retinal thickness substantially changes in one direction. For example, the slope should not be measured from the edge of the primary damage to the opposite side of the lesion at a location of secondary damage. In such an example, the retinal thickness would proceed from a relatively flat surface (e.g., the primary damage site with no retinal tissue) to an inclined surface (e.g., the secondary damage site where the retinal tissue thins from the primary damage site to the periphery). In addition, as persons of ordinary skill in the art understand, the secondary damage caused by a laser is not uniform, and that irregularities in tissue thickness may be evident. Accordingly, the slope is determined by taking a best fit linear regression between two points of the retina. Such adjustments are preferred to account for the irregularities of retinal tissue. Other methods for standardizing the measurements are known in the art. For example, the methods may be practiced by measuring and calculating the average retinal thickness in the lesion site and the surrounding retinal area.

The methods of the invention are useful for quantifying the amount of damage resulting from a focal injury to the retina. Focal injuries result in a discrete area of primary damage indicated by tissue disruption, cell death, and generalized necrosis. Focal injuries may be optical (e.g., as from a laser), chemical, or physical. In addition, the focal injuries may be intended (e.g., surgical procedures) or accidental (e.g., with laboratory or military laser instruments).

After exposure to a laser, the retina experiences numerous changes resulting from the injury. Depending on the degree of injury, determined by, among other things, the intensity and duration of the laser beam exposure, the retina can undergo loss of choriocapillaries and disruption of Bruch's membrane, cell death, some local proliferation of phagocytic cells, edema, and neovascularization (Rosner et al., "Neuroprotective therapy for argon-laser induced retinal injury", *Exp. Eye Res.,* 65:485–495 (1997)). In addition, if the laser intensity is sufficiently strong, a hole in the retina may be generated (Chuang et al., "A traumatic macular hole secondary to a high-energy Nd:YAG laser", *Opthalmic Surgery and Lasers,* 32(1):73–76 (2001)).

In clinical settings, laser treatment may result in some retinal thickening in the first week following treatment, but after the second week following treatment, the retina experiences thinning and scarring. Accordingly, the methods of the invention may be practiced after the first week following treatment, and are preferably practiced after the second week of treatment. In other words, the methods of the invention are preferably practiced after acute inflammation produced by the retinal injury has subsided.

Because the methods of the invention enable in situ quantification of retinal damage caused by focal injuries, the methods provide ways of screening pharmaceutical compositions for potential neuroprotective effects. Neuroprotective agents will act to prevent cell death in retinal tissue, and preferably, will prevent cell death of the retinal ganglion cells, which are responsible for relaying the visual information from the retina to higher order visual centers in the central nervous system, such as the lateral geniculate nucleus of the thalamus.

Pharmaceutical compositions containing neuroprotective agents, or potential neuroprotective agents, as the active compound, may contain the agents in a concentration range of approximately 0.0001% to approximately 10% (weight by volume) and more preferably approximately 0.0005% to approximately 0.5% (weight by volume). In addition, the compositions may comprise preservatives, vehicles, tonicity adjustors, buffers, and antioxidants. Examples of preservatives include, but are not limited to, benzalkonium chloride, chlorobutanol, thimerosal, phenylmercuric acetate, and phenylmercuric nitrate. Suitable vehicles include, but are not limited to, polyvinyl alcohol, povidone, hydroxypropyl methyl cellulose, poloxamers, carboxymethyl cellulose, hydroxyethyl cellulose, and purified water. Examples of tonicity adjustors include, but are not limited to, salts, particularly sodium chloride, potassium chloride, mannitol, and glycerin, or any other suitable ophthalmically acceptable tonicity adjustor. Ophthalmically acceptable buffers include, but are not limited to, acetate buffers, citrate buffers, phosphate buffers, and borate buffers. Acids or bases may be used to adjust the pH the compositions as needed. Examples of ophthalmically acceptable antioxidants include, but are not limited to, sodium metabisulfite, sodium thiosulfate, acetylcysteine, butylated hydroxyanisole, and butylated hydroxytoluene.

Compositions containing neuroprotective agents may be administered as frequently as necessary to maintain a desired concentration or range of concentrations for sufficient time to maintain the beneficial neuroprotective effects. However, those skilled in the art will recognize that the frequency of administration may depend on the nature of the agent and its concentration in the composition. Particular dosages and administration schedules will be determined by the physician prescribing the composition.

By way of example, and not by way of limitation, a neuroprotective agent may be administered to a subject that has been, or will be, exposed to a laser. For example, a patient scheduled to undergo laser photocoagulation treatment may be administered a neuroprotective agent prior to the treatment. Alternatively, a subject injured by a laser may be administered one or more neuroprotective agents as soon as possible after the laser injury to attempt to reduce the spread of secondary, collateral damage. After the subject's retina has been exposed to the laser, the slope of retinal thickness caused by the laser may be measured. The relationship between the slope of retinal thickness of the treated subject (i.e., the subject that received the neuroprotective agent) and the slope of retinal thickness of an untreated subject (i.e., a subject or subjects that have not received neuroprotective agents in connection with laser injuries) will reflect the neuroprotective effects of the agent. An agent that is neuroprotective will prevent secondary cell loss resulting from the injury, and accordingly, the slope of retinal thickness should be steeper than the slope of retinal thickness in untreated subjects, thereby indicating less extensive secondary damage resulting from the laser.

EXAMPLES

The following examples provide those of ordinary skill in the art with specific preferred methods within the scope of the present invention for carrying out the present invention and are not intended to limit the scope of the invention.

Example 1

A 54 year old man presents with a reduced visual field. An ophthalmic examination reveals the presence of a tissue mass on the retina. A biopsy is performed. The tissue is non-malignant; however, enucleation is recommended due to the size of the mass. The patient agrees to participate in clinical trials examining neuroprotective effects of agents for reducing secondary damage caused by laser photocoagulation.

The retinal thickness of the patient's eye is determined using an Optical Coherence Tomography (OCT) Scanner (Humphrey Instruments, Inc., San Leandro, Calif.). Two weeks later, the patient receives a topical ophthalmic solution and is instructed to apply the solution to his eye three times a day. After seven days of treatment, the patient receives laser photocoagulation treatment at random sites in the retina. Four weeks after laser treatment, the thickness of the patient's retina is measured again. The slope of retinal thickness is calculated from a first point at the edge of the primary damage to a second point of the retina that is not injured (i.e., along line A as shown in FIG. 2). A line extending through the two points intersects the center of the lesion site (as shown as lines 10 or 20 in FIG. 1) The slope of retinal thickness is significantly greater than the slope of retinal thickness from untreated, control subjects. The agent in the ophthalmic solution is tested on more subjects to standardize the results.

Example 2

A 57 year old diabetic male with diabetic retinopathy volunteers to participate in clinical trials for potential neuroprotective agents that may reduce secondary, collateral damage resulting from laser photocoagulation treatment. The patient's retina is scanned with a Retinal Thickness Analyzer (Talia Technologies, Ltd., Mevasseret Zion, Israel), and the retinal thickness is measured. The patient receives a week's supply of an ophthalmic solution and is asked to topically apply the solution three times a day for one week. The patient is not aware whether the solution contains the active compounds being tested or if it is a control solution. One week later, the patient receives laser photocoagulation treatment. The patient's retinal thickness is measured at 2, 4, and 6 weeks following treatment. Physicians determine that the slope of retinal thickness resulting from the laser treatment is not significantly affected by the ophthalmic solution (i.e., the slope of retinal thickness does not significantly differ from the slope of retinal thickness for control patients). Similar results are achieved in other patients. The active compound in the ophthalmic solution is not pursued further for neuroprotective effects.

Example 3

A 72 year old woman presents with blurred vision in her right eye with particular distorted images near the middle of her visual field. An ophthalmologist conducts an eye exam. The woman indicates that the lines of an Amsler grid appear distorted. The ophthalmologist detects the presence of an abnormal amount of soft drusen. A diagnosis of age-related macular degeneration (AMD) is made. The physician recommends laser photocoagulation to reduce choroidal neovascularization resulting from the AMD. Retinal scans are performed using the Retinal Thickness Analyzer (Talia Technologies, Ltd., Mevasseret Zion, Israel) before and twenty-one days after laser surgery. The woman is topically administered a composition containing the NMDA receptor antagonist, memantine (0.25% w/v), prior to laser treatment. Retinal thickness analysis after the surgery reveals little secondary damage (e.g., the slope of retinal thickness is large). In particular, the retinal thickness changed by 200 $\mu$m over a distance of about 40 $\mu$m. The slope of damage is approximately 8. The woman continues to receive additional laser treatments without significant visual impairment.

Various publications and/or references have been cited herein, the contents of which, in their entireties, are incorporated herein by reference.

While this invention has been described with respect to various specific examples and embodiments, it is to be understood that the invention is not limited thereto and that it can be variously practiced with the scope of the following claims.

What is claimed is:

1. A method for measuring retinal damage in a subject, the damage results from a focal injury to a retina, the method comprising the step of calculating a slope of retinal thickness between a plurality of locations on the retina having damage, including secondary damage, resulting from a focal injury, wherein the amount of retinal damage correlates to the slope of retinal thickness.

2. The method of claim 1, wherein a greater amount of retinal damage corresponds to a more shallow slope of retinal thickness.

3. The method of claim 1, further comprising the step of administering a neuroprotective agent to the subject.

4. The method of claim 3, wherein the neuroprotective agent is administered to the subject before the retinal injury.

5. The method of claim 3, wherein the neuroprotective effects of the agent correlate with an increased slope of retinal thickness as compared to the slope of retinal thickness in a subject that has not received the neuroprotective agent.

6. The method of claim 1, further comprising measuring retinal thickness in situ.

7. The method of claim 1, further comprising the step of administering a potential neuroprotective agent to the subject.

8. The method of claim 1, wherein the focal injury is caused by a laser directed toward the retina of an eye.

9. A method for measuring retinal damage in a subject, the damage results from a focal injury to a retina, the method comprising the steps of:

measuring the thickness of the retina at a plurality of locations on the retina after inflammation produced by the injury has subsided; and calculating a slope of retinal thickness between the locations, wherein the amount of retinal damage correlates to the slope of retinal thickness.

10. The method of claim 9, wherein a greater amount of retinal damage corresponds to a more shallow slope of retinal thickness.

11. The method of claim 9, wherein the damage includes secondary damage from the focal injury.

12. The method of claim 9, further comprising the step of administering a neuroprotective agent to the subject.

13. The method of claim 12, wherein the neuroprotective agent is administered to the subject before the retinal injury.

14. The method of claim 12, wherein the neuroprotective effects of the agent correlate with an increased slope of retinal thickness as compared to the slope of retinal thickness in a subject that has not received the neuroprotective agent.

15. The method of claim 9, wherein retinal thickness is measured in situ.

16. The method of claim 9, further comprising the step of administering a potential neuroprotective agent to the subject.

17. The method of claim 9, wherein the focal injury is caused by a laser directed toward the retina of an eye.

* * * * *